(12) United States Patent
Hill

(10) Patent No.: US 6,944,889 B2
(45) Date of Patent: Sep. 20, 2005

(54) METHOD OF DISPENSING VOLATILE AND SOLUBLE SUBSTANCES AND A DEVICE FOR USE THEREIN

(75) Inventor: Simon David Julian Hill, West Byfleet (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/968,590

(22) Filed: Oct. 19, 2004

(65) Prior Publication Data

US 2005/0053574 A1 Mar. 10, 2005

Related U.S. Application Data

(62) Division of application No. 10/619,847, filed on Jul. 15, 2003, which is a continuation of application No. PCT/US02/00965, filed on Jan. 14, 2002.

(51) Int. Cl.[7] .............................. E03D 9/02; B01D 11/02
(52) U.S. Cl. ............................ 4/222; 422/264; 422/265
(58) Field of Search ......................... 4/222, 222.1, 223, 4/228.1, 496; 210/198, 200, 220; 422/264, 265, 261

(56) References Cited

U.S. PATENT DOCUMENTS

| | | | |
|---|---|---|---|
| 3,766,576 A | 10/1973 | Ancel | |
| 4,241,025 A | * 12/1980 | Grayson et al. | 422/265 |
| 4,370,763 A | 2/1983 | Dolan | |
| 4,534,070 A | 8/1985 | Hauptmann et al. | |
| 4,763,685 A | * 8/1988 | King, Sr. | 422/265 |
| 5,064,624 A | * 11/1991 | King | 422/264 |
| 5,407,567 A | * 4/1995 | Newhard | 210/198.1 |
| 5,476,116 A | * 12/1995 | Price et al. | 422/264 |
| 5,876,707 A | 3/1999 | Rethke et al. | |
| 6,309,538 B1 | * 10/2001 | Khan | 210/198.1 |

FOREIGN PATENT DOCUMENTS

| | | |
|---|---|---|
| JP | 50006716 A | 1/1975 |
| JP | 56013076 A | 2/1981 |
| JP | 58185513 A | 10/1983 |
| JP | 63099006 A | 4/1988 |
| JP | 06271455 A | 9/1994 |
| JP | 07053349 A | 2/1995 |
| JP | 09141254 A | 6/1997 |
| JP | 10087477 A | 4/1998 |
| WO | WO 99/48469 A1 | 9/1999 |
| WO | WO 99/48539 A1 | 9/1999 |
| WO | WO 00/04215 A2 | 1/2000 |
| WO | WO 00/31385 A1 | 6/2000 |
| WO | WO 00/67704 A2 | 11/2000 |

* cited by examiner

*Primary Examiner*—Tuan Nguyen
(74) *Attorney, Agent, or Firm*—Bridget Murray; Cynthia L. Clay; Jason J. Camp

(57) ABSTRACT

A device (1) for dispensing a volatile substance and simultaneously or sequentially dispensing a soluble substance comprising a structure (2, 3, 4) floatable on a liquid (L). The structure includes a first chamber (5) adapted to receive a filling of a first ingredient (A) adapted to release and diffuse a volatile substance, such as a fragrance, as a result of being contacted with the liquid on which the structure is floated. The structure (1) further includes a second chamber (6) adapted to receive a second ingredient, such as a spa product to be dissolved into the liquid. Floating the device (1) on a liquid such as bath water causes the liquid to contact the first (A) and second (B) ingredients, whereby the volatile substance is released from the first ingredient (A) preferably in the form of a vapour or steam, while the second ingredient (B) is dissolved into the liquid. A preferred application is as a bathing implement or a product for toilet hygiene.

8 Claims, 2 Drawing Sheets

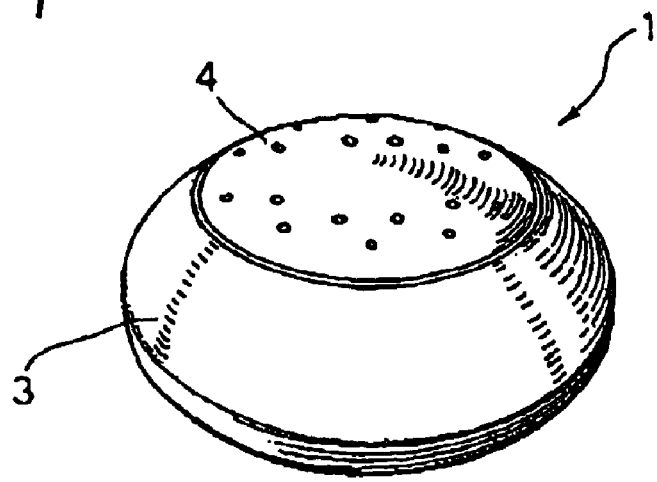
Fig_1
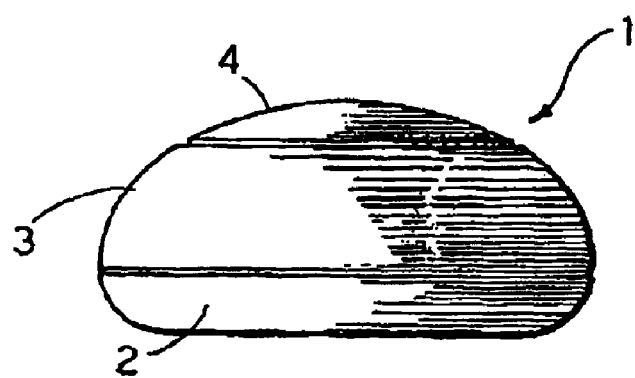
Fig_2
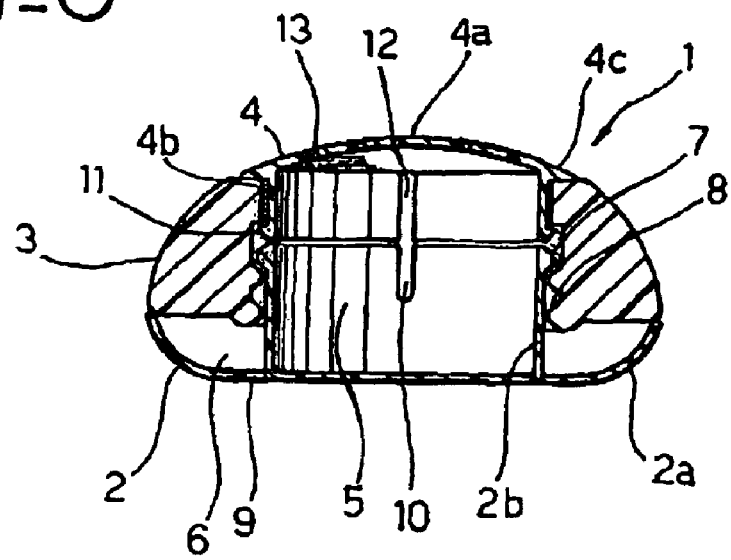
Fig_3

Fig_4
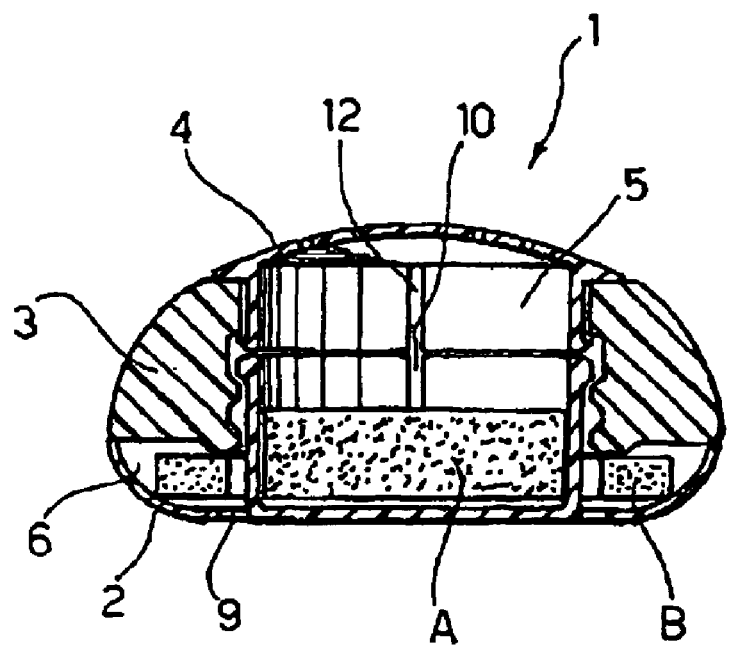
Fig_5
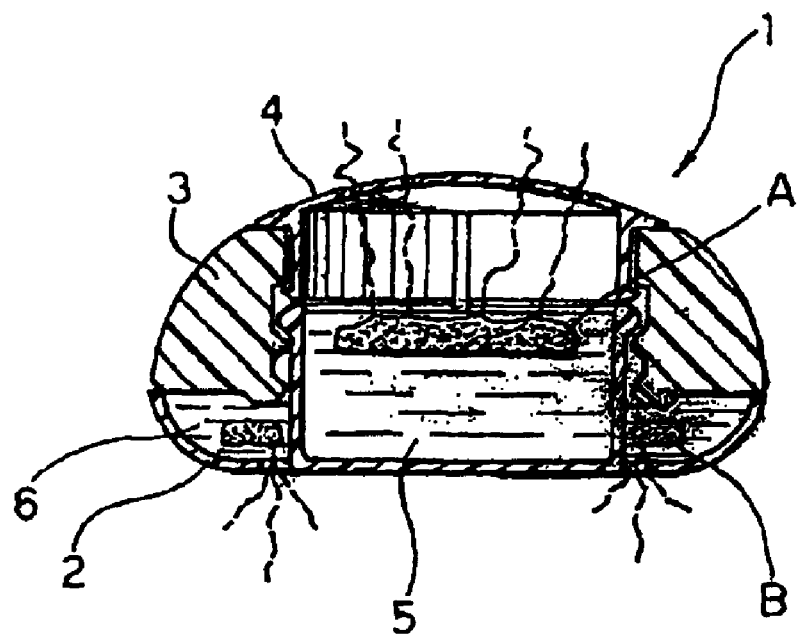

US 6,944,889 B2

METHOD OF DISPENSING VOLATILE AND SOLUBLE SUBSTANCES AND A DEVICE FOR USE THEREIN

CROSS REFERENCE TO RELATED APPLICATION(S)

This application is a divisional of application Ser. No. 10/619,847, filed Jul. 15, 2003, which is a continuation of International Application No. PCT/US02/00965, designating the U.S., filed Jan. 14, 2002.

FIELD OF THE INVENTION

The present invention relates to a method of simultaneously or sequentially dispensing volatile and soluble substances, a device for use therein and its respective package and recharge unit. More particularly this invention relates to a dual action dispensing method, and devices for use therein, which is able to dispense a volatile substance into the atmosphere whilst simultaneously or sequentially dispensing a soluble substance into an aqueous medium. This invention was developed by paying specific attention to its possible use for the dispensing of products for personal care such as bathing products, fragrances, cosmetics, skin treatments and the like. However, even though the following description will be made by primarily referring to the above stated possible use, the scope of the invention is in no way restricted to that specific area and may well include a wide variety of possible uses such as dispensing a wide variety of scented substances including air fresheners, aromatherapy oils, incense and the like; disinfectants; detergents; medicaments; nutrients for both humans and animals; insecticides, pesticides or insect repellents; water purification materials and the like.

BACKGROUND TO THE INVENTION

Surveys of habits and practices data in several countries in the western world has shown that the stress and overload of modern life is driving the need for respite. This is supported by the recent growth in the bath additives, scented candles and aromatherapy markets which promise mental and physical rest and relaxation. As such research has turned to developing a product which is able to transport the consumer to a new level of relaxation.

In line with the consumers' desire for enhanced relaxation there has also been a marked shift in their washing habits and practices. Today showers are generally recognised as a rapid and efficient way to cleanse the body and hair whilst bathing is becoming increasingly popular as a means of personal pampering and relaxation. The act of taking a bath is increasingly seen as a luxury which both men and women are turning to for cosmetic, medical and emotional therapy.

As a result of this divergence in consumer practice different types of products are emerging which are to be used specifically either in the bath or in the shower. Products for use in the bath have moved away from functional cleansing products to products in which the emphasis is placed on their use as relaxing, skin softening, mood enhancing, fragrancing and "pampering".

Various arrangements are well known in the art for generating foams and the like in bathing water. Bath preparations of various kinds have also been proposed which float on the bath water and/or gradually dissolve therein and this enables the benefits of such products to be enjoyed throughout the prolonged bathing time. Such prior art includes JP-10087477-A which discloses a slowly dissolving bath product comprising perfume, moisture agent, plant extract and colouring agent; JP-58185513-A which discloses a floating bath product for fragrancing the bath tub but without fragrancing the human body by encasing a fragrance material within an air permeable but water tight container; JP-06271455-A which discloses a rapidly dissolving bath product comprising sodium carbonate particles, an organic acid and a binder; JP-50006716-A which discloses a floating mould coated in bathing agents, including fragrance, and which dissolves in tepid bath water and JP-07053349-A which discloses a floating bathing agent capable of supporting a fragrance for the purposes of fragrancing bath water or the surrounding environs.

The art also discloses arrangements adapted for diffusing soluble substances in the bathing water. Such disclosures include JP-63099006-A which discloses a sealing bag comprising a bathing agent and which is capable of uniformly diffusing the bathing agent into bath hot water; JP-09141254-A which discloses a synthetic resin mould for deodorising the hot water remaining in the bath; JP-56013076-A which discloses a bath perfuming implement comprising a perfume container associated with the lower part of a floating member and a porous part fitted to the perfume container part wherein the arrangement also includes an oleophilic substance applied to the floating member and adapted to remove dirt comprised of fatty materials floating on the surface of the bath water; and WO 00/67704 which discloses a container suitable for cosmetics, fragrances and the like wherein the container itself is formed from sodium bicarbonate and an acid, or from soap, and which therefore rapidly disperses in bathing water.

Although the prior art provides useful teaching in the field of fragrancing bathing water, or adding bathing additives to the water by means of a floating, or more commonly a slowly dissolving device, there remains a need for a method of being able to simultaneously or sequentially, slowly or rapidly, deliver two or more benefits for the bathing consumer wherein at least one of the benefits is released into the bathing water and at least one of the benefits is released into the atmosphere.

It is therefore an object of the present invention to provide a dual action dispensing method which is able to act at the interface of a liquid with a gas and dispense a volatile substance into the atmosphere whilst simultaneously or sequentially dispensing a soluble substance into the liquid medium. It is a further object of this invention to provide devices for use therein including the respective package and recharge unit. In one specific embodiment of the present invention it is an object to provide an improved solution for the dual dispensing of volatile and soluble personal care products, such as bathing products. Not only does this invention provide a dual action benefit but it also enables the benefits to be delivered over a longer period of time than has been possible to date and enables the delivery of a superior rendition of the fragrance such that more complex, subtle and delicate fragrances can be delivered than has been possible previously.

SUMMARY OF THE INVENTION

The present invention relates to a method for simultaneously or sequentially dispensing volatile and soluble substances including the steps of:

providing a first ingredient (A) adapted to release a volatile substance as a result of being contacted with a liquid, providing a second ingredient (B) adapted to be dissolved in said liquid, associating said first (A) and second (B) ingredients to a structure (1) floatable on said liquid, and floating said floatable structure (1) on said liquid thereby causing said liquid to contact said first (A) and second (B) ingredients, whereby said volatile substance is released from said first ingredient (A) and simultaneously or sequentially said second ingredient (B) is dissolved and released into said liquid, or vice versa whereby said second ingredient (B) is dissolved and released into said liquid and simultaneously or sequentially said volatile substance if released from first ingredient (A).

The present invention also relates to a device adapted for carrying out such a method and the respective package, namely the combination of such a device with products contained therein to be dispensed in volatile/soluble form. Finally, the invention also relates to a recharge unit for such a package.

DETAILED DESCRIPTION OF THE INVENTION

All percentages and ratios used herein are by weight of the total composition and all measurements made are at 25° C., unless otherwise designated. Unless otherwise indicated, all percentages, ratios and levels of ingredients referred to herein are based on the actual amount of the ingredient, and do not include solvent, fillers or other materials which may be combined with the ingredient in commercially available products.

All publications cited herein are hereby incorporated by reference in their entirety, unless otherwise indicated.

The term "fragrance" as used herein means any composition containing one or more synthetic or naturally derived perfume raw materials which may be applied to the human body, or to the animal body or to any suitable carrier material. Such compositions may include combinations of such materials, whether found naturally or blended by a perfumer, and should also be read to encompass products such as pot-pourri, aromatherapy oils and other similar products.

The term "cosmetically-acceptable," as used herein, means that the compositions, or components thereof, are suitable for use in contact with a human or animal surface such as skin or hair without undue toxicity, incompatibility, instability, allergic response, and the like.

The term "medicament" as used herein means a medicine or remedy which is suitable for use in contact with a human or animal surface such as skin or hair without undue toxicity, incompatibility, instability, allergic response, and the like.

The term "soluble" as used herein, means at least about 0.1 g of solute dissolves in 100 ml of solvent at 25° C. and 1 atm of pressure.

The invention will now be described by referring to the enclosed drawings, wherein:

FIG. 1 is a perspective view of a device according to the invention,

FIG. 2 is a side elevational view of the device of FIG. 1,

FIG. 3 is a diametrical cross-sectional view of the device of FIGS. 1 and 2, and FIGS. 4 and 5 are two cross-sectional views substantially corresponding to FIG. 3 which schematically show operation of the device of FIGS. 1 to 3.

In the annexed drawings a device adapted for use in dispensing volatile/soluble substances is generally indicated by reference numeral 1.

Although primarily developed with bathing in mind, many other novel and inventive uses can be envisaged for such a method and device with a dual delivery system which is activated on contact with liquid, especially water. Such uses include, but are not limited to, delivering a fragrance and product with medicinal or cosmetic benefits for use while bathing; delivering a decongestant and a facial soothing product for use as a steam bath during a cold; delivering a fragrance to attract insects and an insecticide for killing them; delivering a fragrance and a disinfectant for use in toilets or swimming pools; for delivering incense and water purification means for use in a font; to deliver nutrition to ponds streams and fish tanks; to deliver water purifying substances to stagnant water sources, for making a hot drink and at the same time producing a strong aroma and the like. However, in each of these cases the principle of the invention remains the same and although various changes and modifications can be effected from the embodiments disclosed herein by way of example they do so without departing from the scope of the invention as defined in the annexed claims. In a preferred possible application, device 1 is intended for use in enhancing the bathing experience by releasing a pleasant aroma into the air and by releasing a spa product into the water. These benefits may be medicinal and or cosmetic in nature. For example, the aroma may work to relieve tension while the product simultaneously released into the bathing water may be a product which pampers the skin via exfoliation or moisturisation effects.

Device

The device is preferably comprised of three parts, namely:
a bottom part 2 adapted to contain the active ingredients to be described in the following,
a middle part 3 moulded e.g. in a rigid foamed plastic (or comprised of materials such as wood, cork, and composites thereof) which provides buoyancy, and
a top part 4 through which any gas and aroma can be released or diffused, e.g. due to its generally apertured structure.

The overall, size, structure and material used to form the device will be dependent upon its specific intended use but in general the device for use herein can have any size or shape. It is preferred that the device 1 for use herein has external dimensions of about 20 cm by about 10 cm by about 10 cm, preferably from about 10 cm by about 8 cm by about 6 cm. It is highly preferred that for the bathing variant that the product is easily held within the palm of the hand and is similarly sized to a bar of soap. However products to be used in smaller volumes of liquid should have similarly smaller dimensions eg those to be used in the toilet or as insect repellents may have dimensions such as 3 cm by 2 cm by 2 cm and conversely those to be used on larger areas of liquid eg ponds or swimming pools should have much larger dimensions eg 100 cm by 100 cm by 100 cm. The shape of the device need not be limited to conventional shapes (eg spheres, discs, cubes etc) but can also have a theme, for example or dolphin or whale. Observation of FIGS. 1 to 3 also shows that the outer walls of parts 2, 3 and 4 are preferably shaped to yield an overall outer shape of device 1 which is substantially free of protrusions, thus rendering the device of the invention easy to manipulate especially for the case when used as a bathing implement.

The device can be made of any material that is suitable but it is important that the device be adapted to float on the liquid such that it is able to deliver simultaneously or sequentially both the benefit to the atmosphere and the benefit to the liquid. Suitable materials include, but are not limited to, polyvinyl acetate, laminates, paper, cork, wood, nutshell and the like. For some uses it will be preferred that the device remains in tact after use such that it can be reused, eg for use in the bath but in other case it will be preferred that the device itself is solubilised after use such that no trace remains eg for use to disinfect a toilet. As such the choice of material will need to be made on a case by case basis and can easily be done by one skilled in the art.

In the exemplary embodiment shown herein, the device comprises a bottom part 2 and a middle part 3 which screw together and a top part 4 is fitted to the middle part 3 via a snap fit design.

The assembled device 1 has therefore the overall shape of a disc (of round or oval shape) including two separate chambers, namely a central chamber 5, which is of substantially cylindrical shape, and an outer, ring shaped chamber 6.

More specifically, bottom part 2 can be seen as comprised of a disc-shaped bottom portion 2a (see FIG. 3) provided with a central cylindrical portion 2b provided at its outer surface (preferably in the vicinity of its upper mouth portion) with formations 7 for screw-like engagement with complementary formations 8 provided in the wall of the inner cavity of middle part 3 which is ring-shaped overall.

A passageway 9, preferably in the form of a plurality of arc-shaped slits, is provided surrounding the base region of portion 2b in order to permit liquid to enter/exit outer chamber 6 as better described in the following.

A further passageway 10, preferably in the form of one or more axial slits provided in the wall of portion 2b and extending axially with respect thereto, is provided in order to enable the liquid onto which device 1 is floated (it is better explained in the following) to enter central chamber 5.

Alternative ways of providing passageways 9 and 10 will be evident to the person skilled in the art. Just to mention one possible alternative, passageways 9 and 10 can be in the form of circular holes in place of slits. Furthermore passageway(s) 10 can be provided (also) in the centre of bottom portion 2a of part 2.

The preferred embodiment shown herein (namely slits 10 extending axially in the wall of portion 2b starting from the mouth rim thereof) is advantageous in that such arrangement may facilitate moderate radial contraction of portion 2b as this is coupled with middle part 3 by screwing of complementary formations 7, 8.

In the presently preferred embodiment, top part 4 is preferably comprised of a dome-shaped web portion 4a from which a peripheral cylindrical portion 4b extends, this latter portion being adapted to be fitted into the central orifice of middle part 3.

Coupling of top part 4 and middle part 3 is preferably achieved by means of a snap fit design including an enlarged rim portion 11 at the lower rim of the wall 4b. Enlarged rim portion 11 is adapted for snap fit engagement into respective annular cavity located at the upper end of engagement formation 8 provided at the wall of inner orifice of middle part 3.

Web portion 4a preferably exhibits an outer rim 4c slightly protruding outwardly of cylindrical portion 4b to abut against the upper end of middle part 3. Radial contraction of top part 4 when engaging middle part 3 is facilitated by further axial slits 12 being provided in wall portion 4b in substantial alignment with slits 10 provided in cylindrical wall portion 2b of bottom part 2.

Finally, reference 13 designate openings provided in the web portion 4a of top part 4 to enable volatile substances generated in inner chamber 5 (as better explained in the following) to be released and diffused into the air. Those skilled in the art will promptly appreciate that the same result can be possibly achieved by different apertured structures e.g. by means of a generally porous structure of portion 4a or parts thereof.

The internal volumes of chambers 5 and 6 could be varied in order to control the amount of the respective product and to control the volume of water received inside them.

Passageway 10 could be more open at the top to allow the user to see the water after it has entered the device.

Active Ingredients

A preferred use of the device shown in FIGS. 1 to 3 provides for two active ingredients designated A and B to be located in inner chamber 5 and outer chamber 6, respectively. The layout of internal compartments 5 and 6 could be varied (e.g. by having chamber 5 intended to receive the ingredient releasing a volatile substance located outwardly with respect to chamber 6 intended to receive the soluble ingredient to be dispensed into the bath).

These active ingredients can be supplied in the form of solids, gels, creams, or liquids and can be supplied in conjunction with the outer body of the device or separately as recharge units. It is highly preferred that they are supplied as solid discs which can easily be inserted into the appropriate chamber of the overall device.

First active ingredient (A): The methods and devices of the present invention comprise a first ingredient A which is adapted to perform an exothermic reaction on contact with water and to release a volatile substance into the surrounding atmosphere. The chemistry of active ingredient A is preferably designed according to the teaching provided in WO-A-99/48539 and WO-A-99/48469. Of course, reference to the solution disclosed in WO-A-99/48539 and WO-A-99/48469 is purely exemplary of an ingredient adapted to release a volatile substance as a result of being contacted with the liquid. Alternative ingredients adapted to find use within the framework of the invention are e.g. effervescent materials which are adapted to release volatile vapours conveying scents and/or therapeutical agents as a result of being contacted with water or another liquid such as the use of sodium bicarbonate and acid mixes.

By way of example it is preferred that ingredient A is produced by adding an aroma oil to a simple mixture of 85% anhydrous citric acid and 15% powdered magnesium. An amount of about 5.9 grams of the mixture will typically heat 50 ml of water to 65° C. Since the amount of fragrance oil is small relative to the rest of the mixture, 0.07 to 0.14 ml of oil can be typically added to 5.9 grams of mixture. Low molecular weight polyethylene glycol (PEG) can be added to the mixture to control the rate of reaction, i.e. small amounts of PEG act to inhibit the reaction and effectively extend the lifetime of the reaction, possibly controlling also the amount of time before releasing of any vapour or steam begins.

Any fragrance can be used for this invention and such a fragrance could be blended from a wide variety of perfume raw materials by those skilled in the art. It is highly preferred that the fragrance chosen is appropriate to the end use of the device such that the aroma enhances and reinforces the benefits of active ingredient B. When the device is to be used as a bathing product the fragrance used can be that of a currently marketed fine fragrance such that the device can be marketed as an ancillary product as part of a fragrance brand.

Second active ingredient (B): The methods and devices of the present invention comprise a second ingredient B which is adapted to be solubilised by the liquid and provide a further benefit to the device user. As previously there are a wide range of materials that can be used as the second ingredient and one skilled in the art would be able to chose an appropriate material dependent upon the desired product benefit. Examples of such materials include, but are not limited to, surfactants or other cleansing materials including detergents, disinfectants including chlorinated materials used in swimming pools, water purifiers, pesticides, insecticides, medicaments useful for topical application such as for the treatment of skin conditions, arthritis, rheumatism or other inflammatory or painful conditions, materials with a skin benefit such as moisturisers, emollients and the like, nutrients, herbal materials, dyes, minerals and the like. It is preferred that in the case of a bathing product the second ingredient is a mild surfactant or has a skin benefit and any commercially available product useful for bathing including those for cleaning such as liquid soaps, bubble baths or bath oils; and those providing a skin moisturising benefit such as Oil of Olay Moisturising Body Wash® and other such moisturising materials would be useful for use herein.

The second ingredient can be in the form of a solid, liquid or gel and should be capable of being solubilised when liquid such as water enters the device. For ingredients which are less soluble the increase in temperature within the device provided by the exothermic reaction with ingredient A can be used to enhance their solubility. It is also possible that the device can be modified such that ingredient B is released only slowly into the surrounding liquid such that the benefit of ingredient B is modified as necessary and or that ingredient B is released in a sustained manner over a period of time up to 1–2 hours. Preferably, for a device for use when bathing, ingredient B will be released over a period of up to 45 minutes, preferably up to 30 minutes and more preferably up to 15 minutes.

Method of Use

In order to activate the device it is necessary firstly to combine the active ingredients with the solid device structure. The device 1 of the invention can be manufactured and sold both as a stand-alone implement and as a package comprised of the device with product(s) A and/or B already provided therein. It is preferred that the device and active ingredients are manufactured separately and that the active ingredients are in the form of solid tablets which enables them to be easily located in the bottom part of device 1 either by the manufacturer or by the consumer. Such a process enables the consumer to recharge the device with further active ingredients and as such it can be suitable for multiple uses. In a further embodiment the device/package itself could be made rechargeable. For example, a bottom part 2 could be sold as a recharge unit containing product(s) A and/or B. In this way, the user would dispose of the bottom part of device by unscrewing after use and substitute therefor such a recharge unit. Alternatively, capsules of products A and/or B could be supplied in the form of a moulded plastic tube that is sealed with laminated film. The act of screwing bottom part 2 to middle part 3 may be caused (in a known manner, e.g. by providing puncturing formations—not shown) extending from top part 4 into chamber 5) to automatically puncture the seal of those capsules as the device 1 is screwed back together to prepare the device 1 ready for use. It is highly preferred that the device comprises two active ingredients, A and B, supplied as solid discs and more specifically, that ingredient A is located in central chamber 5 and ingredient B is located in outer chamber 6. Furthermore since the ingredients A and B are stored and handled within different chambers within the device it is possible to combine materials which have so far not been combined due to incompatibility issues.

Once the device has been charged with two, or more, active ingredients it is floated on the desired liquid surface. FIGS. 3 to 5 shows device 1 floated on a liquid such as bath water. As result of device 1 being floated thereon, water enters both inner chamber 5 (via slits 10 and 12) and outer chamber 2 (via slits 9). Water entering device 1 floods inner chamber 5 thus setting off an exothermic chemical reaction which works to heat the surrounding water. If the chemistry of active ingredient A is preferably designed according to the teaching provided in WO-A-99/48539 and WO-A-99/48469 the water in the inner chamber 5 will be heated from about 40° C. (a typical bath temperature) to 60° C. within about 2 minutes. When used in conjunction with chemistry of active ingredient A according tot he teaching provided in WO-A-99/48539 and WO-A-99/48469 the device will release $H_2$ gas and appear to "steam". This will transports fragrance which is contained in ingredient A out of the disc through the apertures 13 provided in top part 4 and into the air. Preferably the device of the invention would continue to release gas for at least 15 minutes, thus providing both long lasting fragrance and also providing a signal that the device is operating.

Similarly, water penetrates into outer chamber 6 through passageway 9, thus causing ingredient B to be dissolved and flow out of chamber 6 through passageway 9. In this way a soluble product such as a spa product (e.g. a skin treatment product having exfoliation or moisturisation effects) can be added to the bath.

More specifically, in the preferred embodiment of the invention, the device is in the form a disc. As the disc floats, an inner chamber containing a product capsule is flooded with water and this sets off a vigorous exothermic reaction. The disc then releases plumes of gas for about 15 minutes, lifting the aroma into the air. At the same time, water enters through slits in the base, dissolving the bath product contained therein and releasing it into the water. The disc can be easily recharged by replacing the product capsules. Preferably, the chamber out of which gas is released is an inner chamber of the device reaching a temperature of 55–60° C. within about two minutes. The soluble product in the form of e.g. a skin treatment product is released into the bath water within 10 minutes. Still preferably, the device/disc is easily recharged by unscrewing a base portion and replacing the product capsules.

What is claimed is:

1. A package comprising:
   a. a device floatable on a liquid comprising;
      i. a first chamber comprising a first passageway enabling said liquid to enter said first chamber as said device is floated on said liquid and an opening on a top portion enabling a volatile substance to be dispensed from said first chamber, and
      ii. a second chamber associated a second passageway putting said second chamber in fluid flow communication with said device is floated on said liquid; and
   b. a first filling in said first chamber, of a first ingredient adapted to release a volatile substance as a result of been contacted with a liquid, and
   c. a second filling in said second chamber, of a second ingredient adapted to be dissolved in said liquid.

2. The package of claim 1, wherein said first ingredient is a composition producing an exothermic chemical reaction as a result of being contacted by said liquid.

3. The package of claim 1, wherein said first ingredient comprises a reaction control component to selectively control the time over which said first ingredient releases said volatile substance as a result of being contacted with said liquid.

4. The package of claim 1, wherein said first ingredient includes an aroma generating component.

5. The package of claim 4, wherein said aroma generating component is fragrance oil.

6. The package of claim 5, wherein said aroma generating component comprises from about 0.07 ml to about 0.14 ml of fragrance oil.

7. The package of claim 1, wherein said first ingredient includes a mixture of citric acid and powdered magnesium.

8. A recharge unit for the package of claim 1, wherein said recharge comprises a bottom part of said device defining at least a part of said first and said second chambers, said bottom part of said device having associated therewith said first and second fillings of said first and second ingredients.

* * * * *

UNITED STATES PATENT AND TRADEMARK OFFICE
CERTIFICATE OF CORRECTION

PATENT NO. : 6,944,889 B2
DATED : September 20, 2005
INVENTOR(S) : Simon David Julian Hill It is certified that error appears in the above-identified patent and that said Letters Patent is hereby corrected as shown below:

Column 8,
Line 55, "said device" should read -- said liquid as said device --.

Signed and Sealed this

Twenty-second Day of November, 2005

JON W. DUDAS
*Director of the United States Patent and Trademark Office*